United States Patent

Bisagni et al.

[11] Patent Number: 5,407,940
[45] Date of Patent: Apr. 18, 1995

[54] ELLIPTICINE COMPOUNDS

[75] Inventors: E. Bisagni, Orsay, France; R. Jasztold-Howorko, Wrocaw, Poland; G. Atassi, Saint-Cloud; A. Pierre, Marly-le-Roi, both of France

[73] Assignee: ADIR et Compagnie, Courbevoie, France

[21] Appl. No.: 130,627

[22] Filed: Oct. 1, 1993

[30] Foreign Application Priority Data

Oct. 2, 1992 [FR] France .................. 92 11672

[51] Int. Cl.⁶ .................. C37D 471/04; A30K 31/475
[52] U.S. Cl. ........................... 514/285; 546/70
[58] Field of Search .................. 546/70; 514/285

[56] References Cited
PUBLICATIONS

CA 94: 222338 1994 (Rivalle, Heterocycles 38(2) 391–7, 1994).

*Primary Examiner*—Johann Richter
*Assistant Examiner*—Catherine S. Kilby Scalzo
*Attorney, Agent, or Firm*—Gordon W. Hueschen

[57] ABSTRACT

The invention relates to a compound selected from those of formula (I):

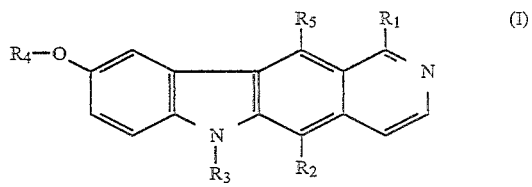

wherein $R_1$, $R_2$, $R_3$, $R_4$ and $R_5$ are as defined in the specification, and medicaments.

6 Claims, No Drawings

ELLIPTICINE COMPOUNDS

The present invention relates to new ellipticine compounds, a process for their preparation and pharmaceutical compositions containing them. The compounds of the present invention are of valuable therapeutic use owing to their anti-tumour activity.

Compounds of the ellipticine family are already known for their anti-cancer properties. For example, the patent application EP-A-42348 may be mentioned in which olivacine compounds were studied. The patent applications EP-A-393575 and EP-A-10029 describe pyrido[4,3-b]carbazole or ellipticine compounds.

Therapeutic needs require the constant development of new anti-cancer agents with the aim of obtaining molecules that are both more active and better tolerated.

The present invention relates to ellipticine compounds which exhibit novelty compared with the compounds described in the prior art: the intensity of the pharmacological properties, that is to say the anti-tumour activity of the compounds of the invention, has been optimised by inserting an aminoalkylaminocarbonyl group into the 1-position of 6H-pyrido[4,3-b]carbazole.

In addition, the compounds of the present invention are distinguished by their greater cytotoxicity in vitro as well as their improved activity in vivo compared with the reference compounds.

The present invention relates more especially to compounds of the general formula (I):

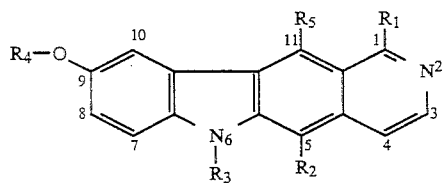

wherein:
$R_1$ represents the radical

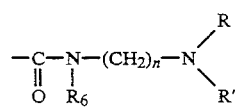

in which:
n is an integer of 1 to 6 inclusive,
R, R' and $R_6$, which are the same or different, are selected, independently of one another, from hydrogen and straight-chain or branched alkyl containing 1 to 6 carbon atoms inclusive optionally substituted by one or more hydroxy, or R and R', together with the nitrogen atom to which they are attached, form a heterocycle optionally containing a second hetero atom, which heterocycle may be substituted by one or more straight-chain or branched alkyl containing 1 to 6 carbon atoms inclusive, and $R_6$ is as defined above, or R and $R_6$ together form a heterocycle which is unsubstituted or substituted by one or more straight-chain or branched alkyl containing 1 to 6 carbon atoms inclusive, and R' is as defined above, $R_2$ represents straight-chain or branched alkyl containing 1 to 6 carbon atoms inclusive, $R_3$, $R_4$ and $R_5$, which are the same or different, are selected, independently of one another, from hydrogen and straight-chain or branched alkyl containing 1 to 6 carbon atoms inclusive, their optical isomers, their possible N-oxides and pharmaceutically-acceptable addition salts with an acid or base.

The heterocycles formed by the radicals R and R' together with the nitrogen atom to which they are attached include more especially pyrrole, pyrrolines, pyrrolidine, imidazole, imidazolines, imidazolidine, pyrazole, pyrazolines, oxazole, oxazolines, oxazolidine, pyridine, piperidine, pyridazine, pyrimidine, pyrazine, piperazine, morpholine and thiomorpholine.

The invention extends also to a process for the preparation of compounds of formula (I) which is characterised by a first biomimetic reaction according to Besselievre Husson (Tetrahedron, (1981), 37, 241–246) in which a compound of formula (II) is reacted in an acid medium, for example in acetic acid, with a compound of formula (III):

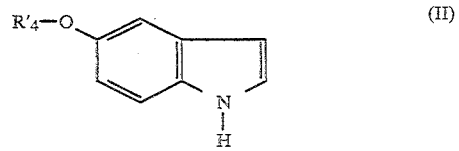

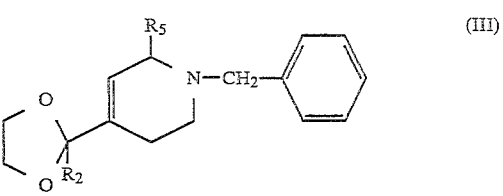

wherein $R_2$ and $R_5$ are as defined for formula (I) and $R'_4$ represents a straight-chain or branched alkyl radical containing from 1 to 6 carbon atoms, to obtain, after debenzylation followed by heating in the presence of a dialkyl oxalate, a compound of formula (IV):

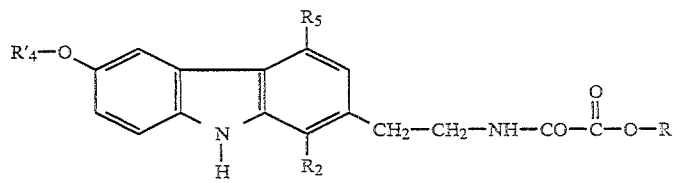

wherein $R_2$, $R'_4$ and $R_5$ are as defined hereinbefore and $R_0$ represents an alkyl group containing from 1 to 5 carbon atoms, which may be cyclised by heating at reflux in the presence of $POCl_3$ in toluene so as to yield, after dehydrogenation on palladium-on-carbon, a compound of formula (Va):

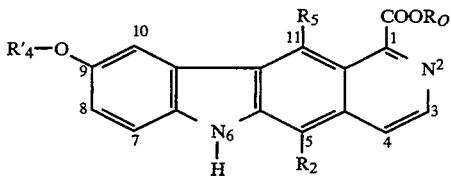 (Va)

wherein $R_0$, $R_2$, $R'_4$ and $R_5$ are as defined hereinbefore, of which, if desired, the 6-nitrogen atom of the carbazole is substituted by treatment with a dialkyl carbonate of formula

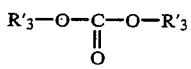

wherein $R'_3$ represents a straight-chain or branched alkyl radical containing from 1 to 6 carbon atoms, in a polar solvent, such as dimethylformamide, in the presence of an alkali metal carbonate, such as potassium carbonate, and a crown ether, to obtain a compound of formula (Vb):

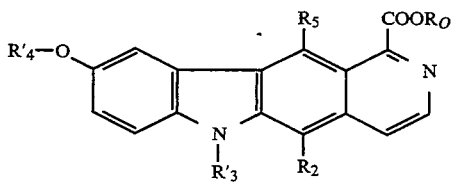 (Vb)

wherein $R_2$, $R'_3$, $R'_4$, $R_5$ and $R_0$ are as defined hereinbefore, the compounds of formulae (Va) and (Vb) forming the totality of the compounds of formula (V):

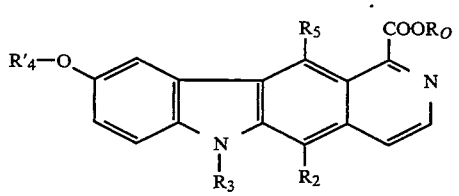 (V)

wherein $R_2$, $R_3$, $R'_4$, $R_5$ and $R_0$ are as defined hereinbefore, which compounds of formula (V) are subjected to a substitution reaction with a compound of formula (VI):

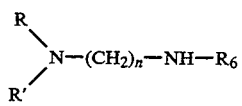 (VI)

wherein R, R', $R_6$ and n are as defined for formula (I), to obtain compounds of formula (Ia):

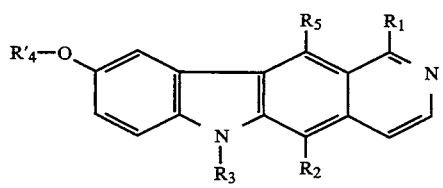 (Ia)

wherein $R_1$, $R_2$, $R_3$, $R'_4$ and $R_5$ are as defined hereinbefore, which compounds of formula (Ia) may be dealkylated by the addition of a boron trihalide, such as boron tribromide, to yield compounds of formula (Ib):

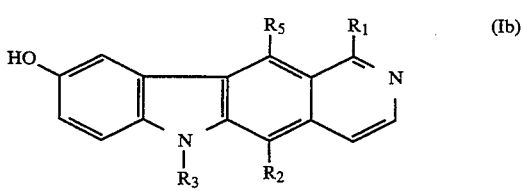 (Ib)

wherein $R_1$, $R_2$, $R_3$ and $R_5$ are as defined hereinbefore, the compounds of formula (Ia) and (Ib) forming the totality of the compounds of the general formula (I) which, where appropriate, may be purified according to a conventional separation technique and, if desired, converted into their possible N-oxides and pharmaceutically acceptable addition salts with an acid or base.

The dealkylation reaction described for the conversion of a compound of formula (Ia) into a compound of formula (Ib) may also be carried out directly on the ester of formula (V) described hereinbefore, so as to obtain a compound of formula (V'):

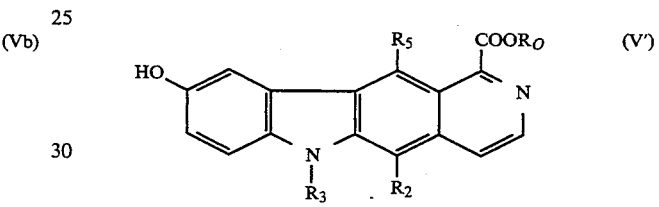 (V')

wherein $R_2$, $R_3$, $R_5$ and $R_0$ are as defined hereinbefore, which is then treated with a compound of formula (VI) as defined hereinbefore, under the same operational conditions as defined for the compound of formula (V), to yield a compound of formula (Ib) as defined hereinbefore.

The compounds of formula (I) possess valuable pharmacological properties. Apart from their greater cytotoxicity in vitro, they prove to be more effective and at least as active in vivo as the compounds taken as reference compounds.

In addition, the compounds described in the present invention are active at very low doses and result in numerous survivors at the optimum doses. They therefore have an excellent therapeutic index.

Owing to their ability to be inserted into DNA and to cause cleavages by inhibiting the topoisomerases, they can be used therapeutically as anti-tumour agents.

The present invention relates also to pharmaceutical compositions containing the compounds of formula (I), their N-oxides, their optical isomers or one of their pharmaceutically-acceptable addition salts with a base or acid, alone or in combination with one or more inert non-toxic excipients or carriers.

Of the pharmaceutical compositions according to the invention there may be mentioned more especially those which are suitable for oral, parenteral, nasal, rectal, perlingual, ocular or respiratory administration, and especially tablets or dragées, sublingual tablets, sachets, paquets, gelatin capsules, glossettes, lozenges, suppositories, creams, ointments, dermal gels, injectable or drinkable preparations, aerosols and eye or nose drops.

The dosage used varies in accordance with the age and weight of the patient, the administration route, and the nature of the therapeutic indication and possible associated treatments, and ranges from 0.1 to 400 mg per day in one or more administrations.

The following Examples illustrate the invention but do not limit it in any way. The starting materials are known or are prepared by known methods of operation.

Preparation of
2-(β-benzylamino)ethyl-6-methoxy-1-methylcarbazole 5-methoxyindole and 1-benzyl-4-(1,1-ethylenedioxyethyl)-1,2,3,6-tetrahydropyridine (boiling point:184°–188° C. at 10 mm Hg, obtained by the reduction of 1-benzyl-4-(1,1-ethylenedioxyethyl)-pyridinium chloride with sodium borohydride in methanol) are heated at reflux for 66 hours in 50% acetic acid. The mixture is then poured into 2 liters of water. After extraction with dichloromethane and removal of the solvent by evaporation, an oily residue is obtained which is subsequently taken up in ethyl acetate. The solid progressively formed is filtered off and washed with the necessary minimum of cold dichloromethane. Colourless acetate crystals are obtained. The corresponding base crystallises in toluene to yield colourless crystals.

Melting point: 150° C.

EXAMPLE 1

1-(N,N-Dimethylaminoethylaminocarbonyl)-5,6-dimethyl-9-hydroxy-6H-pyrido[4,3-b]carbazole

Step A

1-Methyl-2-[(β-ethoxalamido)ethyl]-6-methoxycarbazole 35.6 g (88 mmol) of 2-[(β-benzylamino)ethyl]-6-methoxy-1-methylcarbazole (in the form of the acetate) are dissolved in 400 ml of acetic acid to which 10 g of 10% palladium-on-carbon are added. The mixture is heated to 50° C. and stirred under hydrogen at normal pressure while maintaining the temperature until the theoretical volume of hydrogen has been consumed (10 hours). The solvent is evaporated off under reduced pressure; the residue obtained is taken up in 200 ml of water. After filtration and addition of ammonium hydroxide, the solid is dried in air and recrystallised from toluene. 18.16 g of beige-coloured crystals are obtained.

Yield: 81.4% Melting point: 167°–168° C.

The solid is heated at 100°–110° C. for 1 hour in 70 ml of diethyl oxalate and the mixture obtained is evaporated to dryness. The solid residue is taken up in cyclohexane, filtered and recrystallised from ethyl acetate to yield 23.92 g of the desired compound.

Yield: 94.6% Melting point: 144° C.

| Elemental analysis: $C_{20}H_{22}N_2O_4$ | | | |
|---|---|---|---|
| | C % | H % | N % |
| calculated | 67.78 | 6.26 | 7.91 |
| found | 67.96 | 6.35 | 8.21 |

Step B

Ethyl 1-(3,4-dihydro-9-methoxy-5-methyl-6H-pyrido[4,3-b]carbazolyl)carboxylate 3.54 g (10 mmol) of the amide obtained in Step A are dissolved in 300 ml of boiling toluene and treated dropwise with 30 ml of $POCl_3$. Reflux is maintained for 24 hours. The solvent is evaporated under reduced pressure and the residue is then taken up in 200 ml of water. The solution is filtered and adjusted to pH 9–10 by the addition of sodium carbonate. The resulting solid is washed with water, dried and recrystallised from ethyl acetate. 2.36 g of yellow crystals are obtained.

Yield: 70%. Melting point: 233°–234° C.

| Elemental analysis: $C_{20}H_{20}N_2O_3$ | | | |
|---|---|---|---|
| | C % | H % | N % |
| calculated | 71.41 | 5.99 | 8.33 |
| found | 71.39 | 5.81 | 8.11 |

Step C

Ethyl 1-(9-methoxy-5-methyl-6H-pyrido[4,3-b]carbazolyl)-carboxylate 2.036 g (6 mmol) of the ester obtained in the preceding Step are heated at reflux for 10 minutes in 40 ml of diphenyl ether in the presence of 300 mg of 10% palladium-on-carbon, or for 45 minutes in decaline in the presence of 200 mg of 10% Pd-on-carbon, or for 5 hours in mesitylene in the presence of the same amounts of dehydrogenation agent. The residue is extracted with 1N hydrochloric acid, and the aqueous solution is then neutralised with sodium bicarbonate. The precipitate obtained is extracted with dichloromethane. After evaporation of the solvent, the solid residue remaining is purified by chromatography on a column of silica gel. Elution with dichloromethane results in traces of diphenyl ether. The desired compound is eluted with a 98/2 mixture of dichloromethane and ethyl acetate. The product is recrystallised from ethyl acetate, 1.17 g of yellow crystals are obtained.

Yield: 58.3% Melting point: 255° C.

| Elemental analysis: $C_{20}H_{18}N_2O_3$ | | | |
|---|---|---|---|
| | C % | H % | N % |
| calculated | 71.84 | 5.43 | 8.38 |
| found | 71.75 | 5.54 | 8.45 |

Step D

Ethyl 1-(5,6-dimethyl-9-methoxy-6H-pyrido[4,3-b]carbazolyl)carboxylate

A mixture of 334 mg (1 mmol) of the ester obtained in the preceding Step, 250 mg of dry finely pulverised potassium carbonate, 5 ml of dimethyl carbonate, 1 ml of dimethylformamide and 1 drop of crown ether 18C6 is heated at reflux, with stirring, for 8 hours. After evaporation to dryness the residue is taken up in water. The solid obtained is dried in air and then recrystallised from cyclohexane. 270 mg of yellow crystals are obtained.

Yield: 77.5% Melting point: 162°–164° C.

| Elemental analysis: $C_{21}H_{20}N_2O_3$ | | | |
|---|---|---|---|
| | C % | H % | N % |
| calculated | 72.39 | 5.79 | 8.04 |
| found | 72.16 | 5.91 | 8.03 |

Step E 1-(N,N-Dimethylaminoethylaminocarbonyl)-5,6-dimethyl-9-methoxy-6H-pyrido[4,3-b]carbazole 348 mg (1 mmol) of the ester obtained in the preceding Step are heated in 5 ml of N,N-dimethyl-1,2-diaminoethane for 18 hours. Excess amine is evaporated off under reduced pressure. The residue obtained is taken up in water and the resulting solid is dried in air and recrystallised from cyclohexane. 234 mg of yellow crystals are obtained.

Yield: 60% Melting point: 139° C.

| Elemental analysis: $C_{23}H_{26}N_4O_2$ | | | |
| --- | --- | --- | --- |
| | C % | H % | N % |
| calculated | 70.74 | 6.71 | 14.35 |
| found | 70.53 | 6.96 | 14.35 |

Step F 1-(N,N-Dimethylaminoethylaminocarbonyl)-5,6-dimethyl-9-hydroxy-6H-pyrido[4,3-b]carbazole 390 mg (1 mmol) of the compound obtained in Step E are dissolved in 40 ml of dry dichloromethane under an argon atmosphere. The solution is cooled to −70° C. 10 molar equivalents of boron tribromide, that is 10 ml of a commercial 1M solution in dichloromethane, are added dropwise. The mixture is allowed to return to room temperature (18 hours), and is then poured into 100 ml of iced water. The solution is adjusted to a basic pH by the addition of triethylamine, and then stirred for 3 hours at room temperature. The product is extracted with dichloromethane and the solvent is evaporated off for the purpose of carrying out chromatography on a column of alumina (eluant dichloromethane/ethanol 95/5). The final product crystallises from ethyl acetate which is evaporated off. 164 mg of yellow crystals are obtained.

Yield: 43.6% Melting point: 256° C.

| Elemental analysis: $C_{22}H_{24}N_4O_2$ | | | |
| --- | --- | --- | --- |
| | C % | H % | N % |
| calculated | 70.18 | 6.43 | 14.88 |
| found | 69.79 | 6.69 | 14.49 |

Example 2

1-(N,N-Dimethylaminopropylaminocarbonyl)-5,6-dimethyl-9-hydroxy-6H-pyrido[4,3-b]carbazole This compound is prepared in accordance with the same protocol as that described in Example 1 for Steps A to D.

Step E 1-(N,N-Dimethylaminopropylaminocarbonyl)-5,6-dimethyl-9-methoxy-6H-pyrido[4,3-b]carbazole In Step E the heating time for the ester is set at 8 hours and the diamine used is N,N-dimethyl-1,3-diaminopropane. The product obtained is extracted with dichloromethane; the solvent is then evaporated off and the residue is treated with excess maleic acid in acetone to obtain the corresponding salt.

Step F 1-(N,N-Dimethylaminopropylaminocarbonyl)-5,6-dimethyl-9-hydroxy-6H-pyrido[4,3-b]carbazole 404 mg (1 mmol) of the amide obtained in the preceding Step are dissolved in 40 ml of dry dichloromethane under an argon atmosphere. The solution is cooled to −70° C. 10 molar equivalents of boron tribromide are added dropwise; the mixture is left at room temperature for 18 hours and then poured into 100 ml of iced water. The solution is rendered basic by the addition of triethylamine and stirred at room temperature for 3 hours. The product is extracted with dichloromethane; evaporation of the solvent yields a residue which crystallises in ethyl acetate.

Yield: 76.8% Melting point: 198° C.

| Elemental analysis: $C_{23}H_{26}N_4O_2$, 0.5 $H_2O$ | | | |
| --- | --- | --- | --- |
| | C % | H % | N % |
| calculated | 69.15 | 6.81 | 14.02 |
| found | 69.55 | 6.80 | 13.94 |

Example 3

1-(N,N-Dimethylaminoethylaminocarbonyl)-5,6-dimethyl-9-methoxy-6H-pyrido[4,3-b]carbazole This compound is prepared in accordance with the same protocol as that described in Example 1 with the exception of Step F.

Yield: 60% Melting point: 139° C.

| Elemental analysis: $C_{23}H_{26}N_4O_2$ | | | |
| --- | --- | --- | --- |
| | C % | H % | N % |
| calculated | 70.74 | 6.71 | 14.35 |
| found | 70.53 | 6.96 | 14.35 |

Example 4

1-(N,N-Dimethylaminopropylaminocarbonyl)-5,6-dimethyl-9-methoxy-6H-pyrido[4,3-b]carbazole This compound is prepared in accordance with the same protocol as that described in Example 2 with the exception of Step F.

Yield: 92.5% Melting point: 139° C.

| Elemental analysis: $C_{24}H_{28}N_4O_2$, $2C_4H_4O_4$ | | | |
| --- | --- | --- | --- |
| | C % | H % | N % |
| calculated | 60.37 | 5.70 | 8.80 |
| found | 60.28 | 5.62 | 9.03 |

Example 5

1-(N,N-Dimethylaminopropylaminocarbonyl)-5-methyl-9-methoxy-6H-pyrido[4,3-b]carbazole This compound is prepared in accordance with the same protocol as that described in Example 1 with the exception of Steps D and F, which are not carried out, and with the following modifications to Step E: the amine used is N,N-dimethyl-1,3-diaminopropane, and the solid, after having been dried, is recrystallised from ethyl acetate.

Yield: 93% Melting point: 206° C.

| Elemental analysis: $C_{23}H_{26}N_4O_2, H_2O$ | | | |
|---|---|---|---|
| | C % | H % | N % |
| calculated | 67.72 | 6.91 | 13.72 |
| found | 67.60 | 6.72 | 14.05 |

Example 6

1-(N,N-Dimethylaminoethylaminocarbonyl)-5-methyl-9-hydroxy-6H-pyrido[4,3-b]carbazole This compound is prepared in accordance with the same protocol as that described in Example 1 with the exception of the intermediate Step D and with the following modifications to Steps E and F:

Step E the heating time is set at 8 hours,

Step F as the compound obtained after stirring for 3 hours at room temperature is insoluble in dichloromethane, it is filtered off and recrystallised from ethyl acetate.

Yield: 47% Melting point: >270° C.

| Elemental analysis: $C_{21}H_{22}N_4O_2$ | | | |
|---|---|---|---|
| | C % | H % | N % |
| calculated | 69.59 | 6.12 | 15.46 |
| found | 69.40 | 6.14 | 15.21 |

Example 7

1-(N,N-Dimethylaminopropylaminocarbonyl)-5-methyl-9-hydroxy-6H-pyrido[4,3-b]carbazole This compound is prepared in accordance with the same protocol as that described in Example 1 with the exception of the intermediate Step D and with the following modifications:

Step E the amine used is N,N-dimethyl-1,3-diaminopropane, and the solid obtained is dried in air and recrystallised from ethyl acetate,

Step F the product obtained after stirring for 3 hours is filtered off and recrystallised from ethyl acetate.

Yield: 56% Melting point: 218° C.

| Elemental analysis: $C_{22}H_{24}N_4O_2, 0.5 H_2O$ | | | |
|---|---|---|---|
| | C % | H % | N % |
| calculated | 68.57 | 6.49 | 14.55 |
| found | 68.45 | 6.43 | 14.86 |

Example 8

1-(N,N-Dimethylaminoethylaminocarbonyl)-5-methyl-9-methoxy-6H-pyrido[4,3-b]carbazole This compound is prepared in accordance with the same protocol as that described in Example 1 with the exception of Steps D and F and with the following modification to Step E: The heating time is set at 8 hours.

Yield: 88% Melting point: 215° C.

| Elemental analysis: $C_{22}H_{24}N_4O_2, 0.5 H_2O$ | | | |
|---|---|---|---|
| | C % | H % | N % |
| calculated | 68.57 | 6.49 | 14.54 |
| found | 68.64 | 6.53 | 14.48 |

Example 9

1-[2-(Pyrrolidin-1-yl)ethylaminocarbonyl]-5-methyl-9-methoxy-6H-pyrido[4,3-b]carbazole This compound is prepared in accordance with the same protocol as that described in Example 1 with the exception of Steps D and F, which are not carried out, and the amine used in Step E, which is 2-(pyrrolidin-1-yl)-1-aminoethane.

Example 10

1-[2-(Pyrrolidin-1-yl)ethylaminocarbonyl]-5-methyl-9-hydroxy-6H-pyrido[4,3-b]carbazole This compound is prepared in accordance with the same protocol as that described in Example 6 using 2-(pyrrolidin-1-yl)-1-aminoethane in Step E.

Example 11

1-{2-[(2-Hydroxyethyl)amino]ethylaminocarbonyl}-5,6-dimethyl-9-hydroxy-6H-pyrido-[4,3-b]carbazole

Step A

Ethyl 1-(5,6-dimethyl-9-hydroxy-6H-pyrido[4,3-b]carbazolyl)carboxylate

The ester obtained in Step D of Example 1 is used in the demethylation reaction described in Step F of Example 1 to obtain 1-ethoxycarbonyl-5,6-dimethyl-9-hydroxy-6H-pyrido [4,3-b]carbazole.

Step B

1-{2-[(2-Hydroxyethyl)amino]ethylaminocarbonyl}-5,6-dimethyl-9-hydroxy-6H-pyrido [4,3-b]carbazole 0.4 g (1.198 mmol) of the ester obtained in the preceding Step are dissolved in 10 ml of 2-(2-aminoethylamino)ethanol under an argon atmosphere. The mixture is heated at 120° C. for 24 hours.

Excess amine which has not reacted is removed by placing under a vacuum. Water and dichloromethane are then added to the reaction mixture. The customary treatment of the organic phases yields an oily residue which is taken up in ethanol, and then poured into a saturated solution of ethanol in gaseous hydrogen chloride. The evaporation of the ethanol causes the crystallisation of 0.58 g of the dihydrated dihydrochloride of the desired compound in the form of red crystals.

Yield: 97%

| Elemental analysis: $C_{22}H_{24}O_3N_4, 2HCl, 2H_2O$ | | | | |
|---|---|---|---|---|
| | C % | H % | N % | Cl % |
| calculated | 52.70 | 6.03 | 11.17 | 14.14 |
| found | 52.55 | 5.79 | 10.98 | 17.37 |

Example 12

1-[(4-Aminobutyl)aminocarbonyl]-5,6-dimethyl-9-hydroxy-6H-pyrido[4,3-b]carbazole 0.47 g (1.407 mmol) of the ester obtained in Step A of Example 11 are dissolved in 9 ml of 1,4-diaminobutane under an argon atmosphere. The mixture is heated at 130° for 3 hours.

Excess amine which has not reacted is removed by placing under a vacuum. Water and dichloromethane are then added to the reaction mixture.

The major portion of the insoluble product is isolated by suction-filtering and dried. The other portion is obtained by extraction with dichloromethane and the extract is dried over magnesium sulfate, filtered and then evaporated to dryness.

The total product is recrystallised from absolute ethanol to yield 0.34 g of orange crystals corresponding to the desired compound.

Yield: 62% Melting point: >95° C. (decomposition)

| Elemental analysis: $C_{22}H_{24}N_4O_2$, 0.8 $H_2O$ | | | |
|---|---|---|---|
| | C % | H % | N % |
| calculated | 67.60 | 6.60 | 14.33 |
| found | 67.85 | 6.98 | 13.02 |

Example 13

1-[N-(2-Pyrrolidin-1-ylethyl)aminocarbonyl]-5,6-dimethyl-9-hydroxy-6H-pyrido[4,3-b]carbazole 0.4 g (1.198 mmol) of the ester obtained in Step A of Example 11 are dissolved in 7.5 ml of 1-(2-aminoethyl)-pyrrolidine under an argon atmosphere. The mixture is heated at 120° C. for 16 hours.

Excess amine is removed by placing under a vacuum, and the reaction mixture is hydrolysed. The customary treatment of the organic phase yields 0.341 g of yellow crystals corresponding to the desired compound.

Yield: 65% Melting point: >120° C. (decomposition)

| Elemental analysis: $C_{24}H_{26}N_4O_2$, 2$H_2O$ | | | |
|---|---|---|---|
| | C % | H % | N % |
| calculated | 66.03 | 6.97 | 12.84 |
| found | 65.99 | 7.11 | 12.27 |

Example 14

1-[N-(3-Morpholinopropyl)aminocarbonyl]-5,6-dimethyl-9-hydroxy-6H-pyrido[4,3-b]carbazole 0.36 g (1.078 mmol) of the ester obtained in Step A of Example 11 are dissolved in 10 ml of 4-(3-aminopropyl) morpholine under an argon atmosphere. The mixture is heated at 120° C. for 19 hours.

Excess amine which has not reacted is removed by placing under a vacuum. The reaction mixture is hydrolysed and taken up in dichloromethane.

The mixture is stirred for approximately 1 hour.

The major portion of the insoluble product is isolated by suction-filtering and dried.

The other portion is extracted with dichloromethane and the extract is dried over magnesium sulfate, filtered and evaporated to dryness.

The total product is recrystallised from absolute ethanol to yield 0.42 g of yellow crystals corresponding to the desired compound.

Yield: 90% Melting point: 110° C.

| Elemental analysis: $C_{25}H_{28}N_4O_3$ | | | |
|---|---|---|---|
| | C % | H % | N % |
| calculated | 69.42 | 6.53 | 12.95 |
| found | 69.34 | 6.50 | 12.86 |

Example 15

1-[(N,N-Dimethyl-2-aminoethyl)aminocarbonyl]-5-methyl-6-ethyl-9-hydroxy-6H-pyrido4,3-b]carbazole

Step A

1-Ethoxycarbonyl-5-methyl-6-ethyl-9-methoxy-6H-pyrido[4,3-b]carbazole

To a mixture of 5 g (15 mmol) of the ester obtained in Step C of Example 1, in 10 ml of dimethylformamide, are added 142 ml of diethyl carbonate, 3.75 g of potassium carbonate and 200 mg of crown ether 18C6 under an argon atmosphere. The mixture is heated at 130°-140° C. during 6 days and concentrated. Water and dichloromethane are then added to the reaction mixture. The customary treatment of the organic phase yields 4.11 g of yellow crystals from toluene.

Yield: 76% Melting point: 149° C.

| Elemental analysis: $C_{22}H_{22}N_2O_3$ | | | |
|---|---|---|---|
| | C % | H % | N % |
| calculated | 72.91 | 6.12 | 7.73 |
| found | 73.06 | 6.19 | 7.72 |

Step B

1-Ethoxycarbonyl-9-hydroxy-5-methyl-6-ethyl-6H-pyrido[4,3-b]carbazole 4 g (11.05 mmol) of the ester obtained in the preceding Step are dissolved in 440 ml of dried dichloromethane, under an argon atmosphere, at −78° C. 120 ml (110.5 mmol) of boron tribromide (1M solution in dichloromethane) are added. The mixture is stirred for 2 hours and 30 minutes at −78° C. and then at room temperature during one hour. Excess boron tribromide is hydrolysed by adding drops of water maintaining the temperature at c:a 0° C. The solution is adjusted to a basic pH by the addition of aqueous ammonia and stirred for another 1 hour. The solid obtained is isolated, dried and the organic phase treated in a customary way. The crude product is recrystallised from toluene to yield 2.98 g of the desired compound.

Yield: 78% Melting point: 260° C.

| Elemental analysis: $C_{21}H_{20}N_2O_3$ | | | |
|---|---|---|---|
| | C % | H % | N % |
| calculated | 72.40 | 5.79 | 8.04 |
| found | 72.94 | 5.99 | 7.93 |

Step C

1-[(N,N-Dimethyl-2-aminoethyl)aminocarbonyl]-5-methyl-6-ethyl-9-hydroxy-6H-pyrido[4,3-b]carbazole The mixture formed by 0.8 g (2.30 mmol) of the ester obtained in the preceding Step in 12 ml of N,N-dimethylaminoethylenediamine under an argon atmosphere is heated at 115° C. for 36 hours. The mixture is then hydrolysed, subsequently extracted with dichloromethane, and the organic phase is dried over magnesium sulfate and then filtered. After evaporation of the dichloromethane, the oily residue is purified by chromatography on a column of silica gel (eluant dichloromethane/ethanol 9:1 and approximately 0.5% triethylamine).

0.424 g of yellow crystals corresponding to the desired compound is obtained.

Yield: 44% Melting point: >115° C. (decomposition)

| Elemental analysis: $C_{23}H_{26}N_4O_2$, 1.5 $H_2O$ | | | |
|---|---|---|---|
| | C % | H % | N % |
| calculated | 66.17 | 7.00 | 13.42 |
| found | 66.01 | 6.81 | 13.41 |

Pharmacological Study

The following Examples make it possible to demonstrate that the therapeutic index of the better compounds of the invention is excellent:
they are cytotoxic,
they are active from doses of less than 5 mg/kg up to 30 to 60 mg/kg, and
they produce numerous survivors at the optimum doses.

Example A

Cytotoxicity of the compounds and of the reference compounds

Seven cell lines were used:
2 murine leukaemias, L1210 and P388;
1 human epidermoid carcinoma, KB-3-1, and a human pulmonary carcinoma S1;
the corresponding resistant lines: KB-A1, the multidrug resistance of which was induced by adriamycin (ADR) on KB-3-1; P388/VCR-20, the multidrug resistance of which was induced by vincristine (VCR) on P388; and S1/tMDR, the multidrug resistance of which was obtained by transfecting the human MDR1 gene into S1 cells.

The cells are cultured in complete culture medium RPMI 1640 containing 10% foetal calf serum, 2 mM glutamine, 50 units/ml of penicillin, 50 µg/ml of streptomycin and 10 mM HEPES.

The cells are distributed on microplates and exposed to the cytotoxic compounds. The cells are then incubated for approximately 4 periods of cell doubling, that is 2 days (P 388, P388/VCR-20 and L1210) and 4 days (KB-A1, KB-3-1, S1 and S1/tMDR). The number of viable cells is then quantified by a colorimetric assay, the Microculture Tetrazolium Assay (Carmichael J., DeGraff W. G., Gazdar A. F., Minna J. D. and Mitchell J. R., Evaluation of a tetrazolium-based semiautomated colorimetric assay : assessment of chemosensitivity testing, *Cancer Res.*, 47, 936–942, 1987). The results are expressed as $IC_{50}$, the cytotoxic concentration which inhibits the proliferation of tumour cells by 50%. The results obtained for line L1210 are shown in Table 1:

TABLE 1

| In vitro activity- Line L1210 | |
|---|---|
| Compounds | Cytotoxicity $IC_{50}$, nM |
| ex 1 | 2,6 |
| ex 2 | 4,3 |
| ex 3 | 574,3 |
| ex 4 | 874,7 |
| ex 5 | 1495,0 |
| ex 6 | 3,1 |
| ex 7 | 41,0 |
| ex 8 | 487,0 |
| ex 9 | 1495,5 |
| ex 11 | 29,7 |
| ex 12 | 449,8 |
| ex 13 | 13,1 |
| ex 14 | 10,4 |
| ADR | 26,4 |
| elliptinium acetate | 138,9 |

The results show that the compounds of Examples 1, 2 and 6 are approximately 9 times more cytotoxic than adriamycin and 46 times more cytotoxic than elliptinium acetate.

Example B

Cytotoxicity of the compounds and the reference compounds against lines exhibiting the multidrug resistance phenotype (MDR)

The resistance factor is defined by the ratio:

$$\frac{IC_{50} \text{ sensitive line}}{IC_{50} \text{ resistant line}}$$

TABLE 2

| Cytotoxicities and resistance factors | | | | | |
|---|---|---|---|---|---|
| | Cytotoxicity, $IC_{50}$ (nM) resistance factor | | | | |
| Lines | ex 1 | ex 2 | ex 6 | ADR | Elliptinium acétate |
| sensitive P388 | 5 | 11 | 19 | 20 | — |
| résistant P388/VCR-20 | 4 | 38 | 10 | 340 | — |
| resistance factor | 0,8 | 3,4 | 0,5 | 17 | — |
| sensitive KB-3-1 | 12 | 19 | 20 | 5 | 226 |
| résistant KB-A1 | 120 | 1217 | 737 | 6869 | 4322 |
| resistance factor | 10 | 64 | 37 | 1374 | 19 |
| sensitive S1 | 49 | 57 | 42 | 36 | — |
| résistant S1/tMDR | 25 | 38 | 29 | 135 | — |
| resistance factor | 0,5 | 0,7 | 0,7 | 3,8 | — |

The increased resistance of the resistant lines to the compounds is far weaker than the resistance to adriamycin. The activity of the compounds against KB-A1 is far greater than that of adriamycin or elliptinium acetate. The resistant lines P388/VCR-20 and S1/tMDR (the resistance to ADR of which is weaker) are more sensitive to Examples 1 and 6 than the corresponding sensitive lines. Those compounds could therefore be used against tumours that are resistant to adriamycin.

Example C

In vivo activity

Example C-1

Anti-tumour activity of the compounds against leukaemia P388

Line P388 (murine leukaemia) was supplied by the National Cancer Institute (NCI) (Frederick, USA). The tumour cells ($10^6$ cells) were inoculated on day 0 into the peritoneal cavity of female BDF1 mice (Iffa-Credo, France). Eight to ten mice, of a weight ranging from 18 to 20 g, are used for each experimental group.

The compounds were administered on day 1 via the intraperitoneal route at the doses indicated.

The anti-tumour activity is expressed as a T/C %:

$$\% \ T/C = \frac{\text{Median survival time of treated animals}}{\text{Median survival time of control animals}} \times 100$$

Animals that have survived 60 days (long-term survivors) are indicated.

The results are shown in the following Table 3:

TABLE 3

| Compounds | Dose (mg/kg) | T/C (%) | Survivors on d60/total no. of mice |
|---|---|---|---|
| Example 1 | 5 | 163 | 1/10 |
|  | 10 | 183 | 1/10 |
|  | 20 | 220 | 2/10 |
|  | 30 | 200 | 3/10 |
|  | 60 | 257 | 3/10 |
| Example 2 | 5 | 177 | 0/10 |
|  | 10 | 190 | 0/10 |
|  | 20 | 250 | 3/10 |
|  | 30 | 204 | 1/10 |
|  | 40 | 219 | 2/10 |
|  | 50 | 222 | 3/10 |
|  | 60 | 248 | 3/10 |
| Example 6 | 5 | 280 | 4/10 |
|  | 10 | 233 | 3/10 |
|  | 20 | >600 | 5/10 |
|  | 30 | >600 | 7/10 |
| ADR | 10 | 290 | 2/10 |
| elliptinium acetate | 5 | 171 | 0/10 |

The compounds were tested at equitoxic doses. The gravimetric variation, at the optimum dose used for the compounds, is from −0.4 to −0.7 g, whilst it is −0.7 g for adriamycin and −4 g for elliptinium acetate.

The compounds are active at 5 mg/kg and above, all the doses employed giving long-term survivors for two compounds (Examples 1 and 6 of Table 2). The compound of Example 1 used in a single administration of 30 mg/kg cures 7 out of 10 treated mice whilst adriamycin cures only 2 and ellipitinium acetate cures none. The three compounds tested are considerably more active than ellipitinium acetate which, moreover, is toxic at 5 mg/kg and above.

Example C-2

Anti-tumour activity of the compounds against Lewis pulmonary carcinoma

Lewis pulmonary carcinoma (supplied by NCI, Frederick, USA) was inserted in the form of fragments on d0 and by the subcutaneous route into female B6D2F1 mice weighing 18 to 20 g. The compounds were administered at the doses indicated by the i.v. route on d3, d6 and d9.

The anti-tumour activity was determined on d20 by measuring the tumour volume:

$$\frac{T/C}{\% \ (\text{volume})} = \frac{\text{median tumour volume of treated animals}}{\text{median tumour volume of control animals}} \times 100$$

and by the prolongation of the survival of the treated groups, expressed as T/C %. The long-term survivors (d90) are recorded.

$$\frac{T/C}{\% \ (\text{survival})} = \frac{\text{median survival time of treated animals}}{\text{median survival time of control animals}} \times 100$$

The compound of Example 1 is very active against this very resistant model. A dose of 40 mg/kg is curative for 100% of the animals whilst adriamycin, at the maximum tolerated dose, is far less active (Table 4).

TABLE 4

Anti-tumour activity of the compounds against Lewis carcinoma

| Compound | Dose (mg/kg) | route | median T/C, % (volume) d20 | median T/C, % (survival) | Survivors on d90 |
|---|---|---|---|---|---|
| Control ex. 1 | — | i.v. | 100 | 100 | 1/25 |
|  | 20 | i.v. | 1 | >300 | 6/10 |
|  | 40 | i.v. | 0 | >300 | 10/10 |
|  | 60 | i.v. | 0 | >300 | 6/10 |
| ADR | 2,5 | i.v. | 63 | 108 | 0/10 |
|  | 5 | i.v. | 44 | 125 | 2/10 |
|  | 10 | i.v. | 1 | 128 | 3/10 |

Example C-3

Anti-tumour activity of the compounds against M5076 sarcoma

M5076 sarcoma is supplied by NCI (Frederick, USA). The tumour cells ($10^7$ cells/animal) were inoculated on d0 into the peritoneal cavity of female B6D2F1 mice. The compounds were administered by the i.p. route on d1, d5, d9 and d13 at the doses indicated. The surviving animals on d90 were recorded and the T/C survival (%) was calculated.

The compound of Example 1, at a dose of 20 mg/kg, is very active against that tumour. 6 survivors out of 10 are observed on d90. Ellipitinium acetate is not very active at the maximum tolerated dose (2 mg/kg)—no animal has survived. The results are reproduced in Table 5.

TABLE 5

Anti-tumour activity of the compounds against M5076 sarcoma.

| Compound | Dose (mg/kg) | route | median T/C, % (survival) | Survivors on d90 |
|---|---|---|---|---|
| Control ex. 1 | — | i.p. | 100 | 0/32 |
|  | 5 | i.p. | 168 | 0/10 |
|  | 10 | i.p. | 301 | 4/10 |
|  | 20 | i.p. | >352 | 6/10 |
| ADR | 5 | i.p. | 320 | 4/10 |
| ellipt. ac. | 1 | i.p. | 153 | 1/10 |
|  | 2 | i.p. | 180 | 0/10 |

Example C-4

Anti-tumour activity of the compounds against colon 38

Colon 38 (supplied by NCI, Frederick, USA) was inserted in the form of fragments by the subcutaneous route into female B6D2F1 mice. The compounds were administered by the i.v. route on d2 and d9 and the anti-tumour activity was determined on d25 by measuring the tumour volume (T/C volume, %).

The compound of Example 2, administered by the i.v. route is very active against that solid tumour at a dose of 20 mg/kg and above (T/C=0%) (Table 6). It is as active as 5-fluorouracyle (5-Fu) used at a dose of 80 mg/kg.

TABLE 6

| Anti-tumour activity of the compounds against colon 38 | | | |
|---|---|---|---|
| Compound | Dose (mg/kg) | Route | median T/C, % (tumour volume) |
| ex. 1 | 20 | i.v. | 41 |
|  | 40 | i.v. | 16 |
|  | 60 | i.v. | 0 |
| ex. 2 | 20 | i.v. | 0 |
|  | 40 | i.v. | 0 |
|  | 60 | i.v. | 0 |
| ex. 6 | 10 | i.v. | 35 |
|  | 20 | i.v. | 22 |
|  | 30 | i.v. | 0 |
| ADR | 15 | i.v. | 0 |
| 5-Fu | 80 | i.v. | 0 |

We claim:

1. A compound selected from those of formula (I):

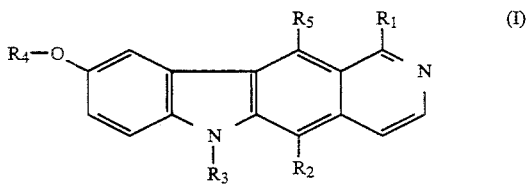

wherein:

$R_1$ represents the group

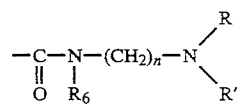

in which:

n is an integer of 1 to 6 inclusive,

R, R' and $R_6$, which are the same or different, are selected, independently of one another, from hydrogen and straight-chain or branched alkyl having 1 to 6 carbon atoms inclusive optionally substituted by one or more hydroxy, $R_2$ represents straight-chain or branched alkyl having 1 to 6 carbon atoms inclusive, $R_3$, $R_4$ and $R_5$, which are the same or different, are selected, independently of one another, from hydrogen and straight-chain or branched alkyl having 1 to 6 carbon atoms inclusive, its optical isomers, its possible N-oxides, and pharmaceutically-acceptable addition salts thereof with an acid or base.

2. A compound according to claim 1 which is selected from 1-(N,N-dimethylaminoethylaminocarbonyl)-5,6-dimethyl-9-hydroxy-6H-pyrido [4,3-b]carbazole, its N-oxides, and its pharmaceutically-acceptable addition salts with an acid.

3. A compound according to claim 1 which is selected from 1-(N,N-dimethylaminopropylaminocarbonyl)5,6-dimethyl-9-hydroxy-6H-pyrido [4,3-b]carbazole, its N-oxides, and also its pharmaceutically-acceptable addition salts with an acid.

4. A compound according to claim 1 which is selected from 1-(N,N-dimethylaminoethylaminocarbonyl)-5-methyl-9-hydroxy-6H-pyrido [4,3-b]carbazole, its N-oxides and also its pharmaceutically-acceptable addition salts with an acid.

5. A method for treating an animal or human living body afflicted with a disease requiring anti-tumor agents inhibiting topoisomerases, resulting from cancer, comprising the step of administering to said living body an amount of a compound of claim 1 which is suitable for alleviation of said disease.

6. A pharmaceutical composition useful in inhibiting topoisomerases which contains as active ingredient an effective amount of a compound according to claim 1, in combination with one or more pharmaceutically-acceptable excipients or vehicles.

* * * * *

UNITED STATES PATENT AND TRADEMARK OFFICE
CERTIFICATE OF CORRECTION

PATENT NO. : 5,407,940
DATED : April 18, 1995
INVENTOR(S) : E. Bisagni, R. Jasztold-Howorko, G. Atassi, A. Pierre It is certified that error appears in the above-indentified patent and that said Letters Patent is hereby corrected as shown below:

```
Column 10, line 29; insert "}-" at the end of the line.
Column 10, line 30; delete the "}-" at the beginning of the
      line.
Column 12, line 16; "4,3-b]" should read -- [4,3-b] --
Column 16, line  8; delete the "(" at the end of the line.
Column 16, line  9; insert "(" at the beginning of the line to
      make it read -- (d90) --
Column 18, line 25; delete the word "also" (Prel. Amdt. 10-1-93)
Column 18, line 30; insert a comma "," after the word "N-oxides"
      and delete the word "also" (Prel. Amdt. 10-1-93)
```

Signed and Sealed this

Twenty-seventh Day of June, 1995

Attest:

BRUCE LEHMAN

Attesting Officer    Commissioner of Patents and Trademarks